United States Patent
Guo et al.

(10) Patent No.: US 11,633,296 B2
(45) Date of Patent: Apr. 25, 2023

(54) VASCULAR SHUNT FRAME AND VASCULAR STENT WITH IMPROVED APPOSITION

(71) Applicant: HANGZHOU ENDONOM MEDTECH CO. LTD., Zhejiang (CN)

(72) Inventors: Wei Guo, Zhejiang (CN); Yongsheng Wang, Zhejiang (CN); Anwei Li, Zhejiang (CN); Liman Shang, Zhejiang (CN)

(73) Assignee: Hangzhou ENDONOM MEDTECH CO. LTD., Hangzhou (CN)

( * ) Notice: Subject to any disclaimer, the term of this patent is extended or adjusted under 35 U.S.C. 154(b) by 0 days.

(21) Appl. No.: 16/765,002

(22) PCT Filed: Nov. 20, 2018

(86) PCT No.: PCT/CN2018/116545
§ 371 (c)(1),
(2) Date: May 18, 2020

(87) PCT Pub. No.: WO2019/101078
PCT Pub. Date: May 31, 2019

(65) Prior Publication Data
US 2020/0315820 A1    Oct. 8, 2020

(30) Foreign Application Priority Data

Nov. 24, 2017   (CN) .......................... 201711192775.3
Nov. 24, 2017   (CN) .......................... 201711192781.9
Aug. 8, 2018    (CN) .......................... 201810899831.5

(51) Int. Cl.
A61F 2/07    (2013.01)
A61F 2/82    (2013.01)
(Continued)

(52) U.S. Cl.
CPC .............. *A61F 2/848* (2013.01); *A61F 2/07* (2013.01); *A61F 2/915* (2013.01);
(Continued)

(58) Field of Classification Search
CPC .................... A61F 2002/061; A61F 2002/067
See application file for complete search history.

(56) References Cited

U.S. PATENT DOCUMENTS

| 6,585,756 B1 | 7/2003 | Strecker |
| 2005/0010277 A1 | 1/2005 | Chuter |

(Continued)

FOREIGN PATENT DOCUMENTS

| CN | 1870951 A | 11/2006 |
| CN | 102014791 A | 4/2011 |

(Continued)

OTHER PUBLICATIONS

The Supplementary European Search Report issued corresponding to EP Application No. EP18880850 dated Dec. 10, 2020.

(Continued)

*Primary Examiner* — Leslie Lopez

(57) ABSTRACT

A vascular shunt frame with improved apposition including a main body tube; at least one end of the main body tube is provided with a sealing covering; the sealing covering is provided with a main blood flow opening; a shaping component is disposed at the edge of the main blood flow opening. When the main body stent is inserted into the main blood flow opening of the main body tube, the shaping component can be closely attached to the outer surface of the main body stent, such that the sealing covering closely fits the outer surface of the main body stent to prevent endoleaks. The present disclosure also provides a vascular stent provided with an apposition-improved vascular shunt frame.

20 Claims, 5 Drawing Sheets

(51) Int. Cl.
*A61F 2/06* (2013.01)
*A61F 2/848* (2013.01)
*A61F 2/915* (2013.01)

(52) U.S. Cl.
CPC ... *A61F 2002/061* (2013.01); *A61F 2002/825* (2013.01); *A61F 2002/8486* (2013.01); *A61F 2002/91575* (2013.01); *A61F 2250/0098* (2013.01)

(56) References Cited

U.S. PATENT DOCUMENTS

| | | | |
|---|---|---|---|
| 2006/0184228 A1 | 8/2006 | Khoury | |
| 2008/0109066 A1* | 5/2008 | Quinn | A61F 2/07 623/1.13 |
| 2009/0177265 A1 | 7/2009 | Dierking et al. | |
| 2011/0270379 A1 | 11/2011 | Bruszewski | |
| 2014/0135905 A1 | 5/2014 | Hung et al. | |
| 2014/0277335 A1 | 9/2014 | Greenberg et al. | |
| 2015/0057737 A1 | 2/2015 | Ondersma et al. | |
| 2015/0209163 A1* | 7/2015 | Kelly | A61F 2/07 623/1.11 |
| 2016/0278910 A1 | 9/2016 | Kelly | |
| 2017/0000630 A1 | 1/2017 | Shames et al. | |
| 2019/0380851 A1* | 12/2019 | Bertini | A61F 2/86 |

FOREIGN PATENT DOCUMENTS

| | | |
|---|---|---|
| CN | 105213076 A | 1/2016 |
| CN | 105228561 A | 1/2016 |
| CN | 105662650 A | 6/2016 |
| CN | 106109056 A | 11/2016 |
| CN | 106456314 A | 2/2017 |
| CN | 205924245 U | 2/2017 |
| CN | 106687074 A | 5/2017 |
| WO | 2008021557 A1 | 2/2008 |
| WO | 2014172501 A2 | 10/2014 |
| WO | 2016154502 A1 | 9/2016 |

OTHER PUBLICATIONS

The Supplementary European Search Report issued corresponding to EP Application No. EP18882101 dated Dec. 1, 2020.
The International Search Report issued corresponding to International Application No. PCT/CN2018116542 dated Jan. 23, 2019.
The International Search Report issued corresponding to International Application No. PCT/CN2018116544 dated Feb. 18, 2019.
The International Search Report issued corresponding to International Application No. PCT/CN2018116546 dated Feb. 18, 2019.
International Search Report issued in International Application No. PCT/CN2018/116545, dated Jan. 30, 2019, pp. 1-2, State Intellectual Property Office of the P.R. China, Beijing, China.
International Search Report issued in International Application No. PCT/CN2018/116543, dated Feb. 26, 2019, pp. 1-2, State Intellectual Property Office of the P.R. China, Beijing, China.
Chinese First Search Report issued in Chinese Application No. 201810899831 5, p. 1, State Intellectual Property Office of the P.R. China, Beijing, China.
Chinese Office Action issued in Chinese Application No. 201810899831 5, pp. 1-5, State Intellectual Property Office of the P.R. China, Beijing, China.
The second Office Action issued corresponding CN application No. 201810899831.5 dated Jul. 7, 2020.

* cited by examiner

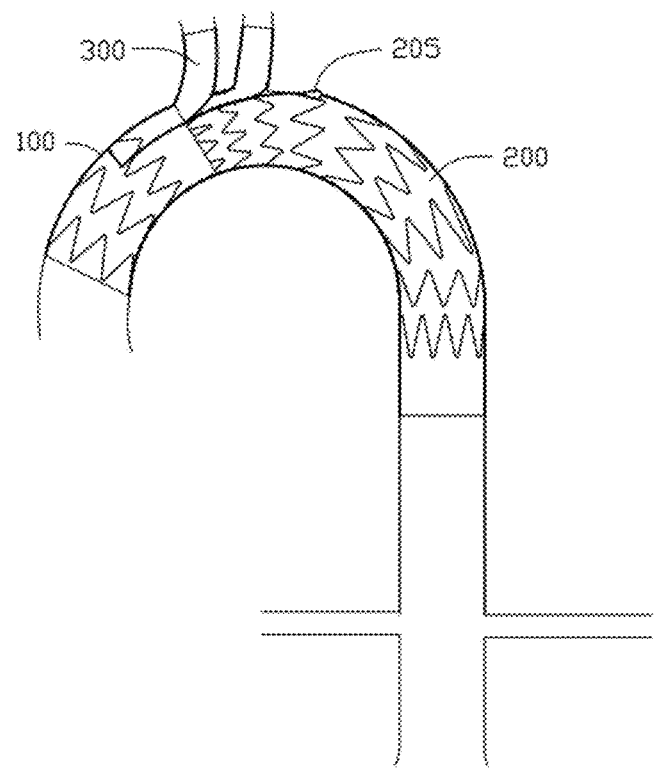
FIG. 24
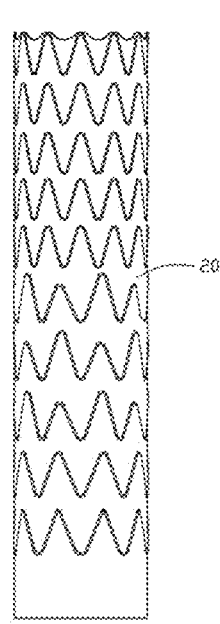 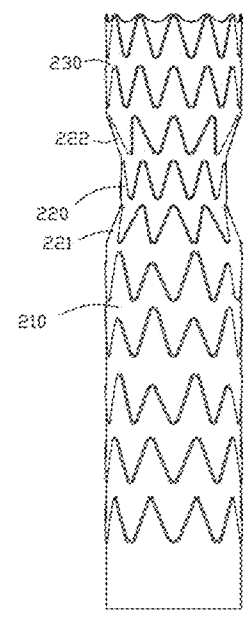 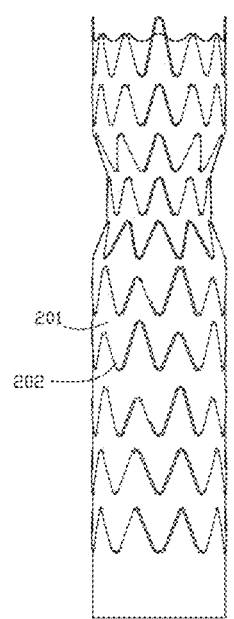 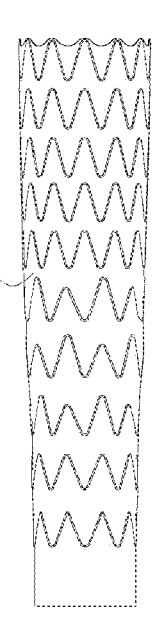
FIG. 25a  FIG. 25b  FIG. 25c  FIG. 25d

VASCULAR SHUNT FRAME AND VASCULAR STENT WITH IMPROVED APPOSITION

CROSS REFERENCE TO RELATED APPLICATIONS

This application is the National Stage filing under 35 U.S.C. 371 of International Application No. PCT/CN2018/116545, filed on Nov. 20, 2018 and published as WO2019101078A1, which claims the priority and benefit of Chinese Application CN 201711192775.3, filed on Nov. 24, 2017, Chinese Application CN 201711192781.9, filed on Nov. 24, 2017, and Chinese Application CN 201810899831.5, filed on Aug. 8, 2018. The contents of all afore-mentioned applications are hereby incorporated by reference in their entireties.

TECHNICAL FIELD

The present disclosure relates to the technical field of implantable blood vessels, and particularly to a vascular shunt frame for improving apposition and a vascular stent provided with the vascular shunt frame.

BACKGROUND

Aortic aneurysm refers to the local or diffusive abnormal expansion of the aortic wall, which causes symptoms due to compression of surrounding organs, and its main danger is tumor rupture. It usually occurs in the ascending aorta, aortic arch, descending thoracic aorta, thoracoabdominal aorta, and abdominal aorta. Aortic aneurysms can be divided into true aortic aneurysms and pseudo aortic aneurysms by structure. The aortic aneurysm causes an increase in the inner pressure of the blood vessel, so it is progressively enlarged. If it develops for a long time, it eventually ruptures. Larger tumors are more likely to rupture. According to statistics, without surgery, 90% of thoracic aortic aneurysms patients die within 5 years, and 75% of abdominal aortic aneurysms patients die within 5 years.

Aortic dissection is another serious aortic disease. Aortic dissection refers to the destruction of the thoracic aorta medial membrane, bleeding in the vessel wall, and blood entering between the medial and adventitia of the vessel wall. Due to the impact of blood flow, once the aortic dissection is formed, the tear can be extended in the direction of blood flow, the dissection and the false lumen are enlarged, and the true lumen is compressed. Therefore, the dangers that may occur in patients with aortic dissection include: (1) the threat of complete rupture of the blood vessel, and once the blood vessel is completely ruptured, the mortality rate is extremely high; (2) the dissection is gradually enlarged, and the true lumen is compressed, so that the blood vessel supplied at the distal end is decreased. In most cases, aortic dissection is secondary to or coexisting with aortic aneurysm. The Oxford vascular disease study in the UK shows that the incidence of aortic dissection in natural populations is about 6/100,000 per year, with more men than women, with an average age of onset of 63 years. The incidence of aortic dissection in China is much higher than that in European and American countries, and the age of onset is relatively young.

Aortic diseases may involve branch arteries. Once branch arteries are involved, it will be difficult to solve them through interventional methods. At present, endovascular treatment of aortic disease has been carried out at home and abroad, that is, a minimally invasive method, which involves implanting a vascular stent into a lesioned artery through a vascular lumen to treat an arterial disease and improve blood supply, thereby achieving the purpose of treatment. The arterial blood vessel stent in the blood vessel lumen is composed of a tubular rigid wire stent and a polymer film fixed on the outside of the tubular rigid wire stent. The tubular rigid wire stent is made by folding elastic rigid wires in a Z shape to be enclosed into a ring, and then stitching or gluing multiple rings with a polymer film to form a stent graft. When used, the stent graft is compressed axially and loaded into a delivery device, and the delivery device passes the smaller femoral artery, the iliac artery, and the brachial artery to reach the lesioned artery, and then the stent graft is released. Due to the elastic force of the metal wire stent, it is automatically restored to a straight tube and is closely attached to the inner wall of the aorta, which separates the lesioned artery from blood flow, thereby achieving the purpose of treatment.

In the prior art, commonly used stents involving arterial branch therapy include chimney stents, integrated multi-branch stents, and window-type stents. These stents are limited by the structure of the stents, often require temporary customization, or are prone to problems such as endoleaks. In addition, the split-type stent composed of multiple modules includes a plurality of shunts that can be connected to the branch stent separated by a covering, and a sealing covering is disposed on an end face of the stent graft away from the heart to prevent endoleaks from occurring between multiple shunts on the end face. However, since the material of the sealing covering is relatively soft, the connection between the vascular stent inserted into the shunt opening and the sealing covering is not tight enough, and it is prone to endoleaks.

SUMMARY

The purpose of the present disclosure is to provide a vascular shunt frame with improved apposition capable of preventing endoleaks, and a vascular stent provided with the vascular shunt frame.

In order to solve the above technical problems, the present disclosure provides a vascular shunt frame with improved apposition. It includes a main body tube, at least one end of the main body tube is provided with a sealing covering; the sealing covering is provided with a main blood flow opening, and an edge of the main blood flow opening is provided with a shaping component.

The present disclosure also provides a vascular stent, which includes a main body stent and a vascular shunt frame. The vascular shunt frame includes a main body tube, at least one end of the main body tube is provided with a sealing covering; the sealing covering is provided with a main blood flow opening, and an edge of the main blood flow opening is provided with a shaping component. One end of the main body stent passes through the main blood flow opening on the sealing covering and is inserted into the main body tube of the vascular shunt frame; the shaping component positions the main body stent such that the sealing covering closely adheres to an outer surface of the main body stent.

The vascular shunt frame with improved apposition with the wall of the aorta provided by the present disclosure, by disposing a shaping component at the edge of the main blood flow opening of the sealing covering of the main body tube, the sealing covering is positioned. When the main body stent is inserted into the main blood flow opening of the main body tube, the shaping component can be closely attached to the outer surface of the main body stent, so that the sealing covering and the outer surface of the main body stent can be closely fit to prevent endoleaks.

BRIEF DESCRIPTION OF THE DRAWINGS

In order to more clearly illustrate the technical solution of the embodiments of the present disclosure, the drawings used in the embodiments are briefly introduced below. Obviously, the drawings in the following description are some embodiments of the present disclosure. Those of ordinary skill in the art can also obtain other drawings according to these drawings without creative efforts.

FIG. 24 is a schematic diagram of a vascular stent in another operating state in accordance with an eighteenth embodiment of the present disclosure.

FIG. 25a is a schematic structural view of a main body stent of a vascular stent in accordance with a nineteenth embodiment of the present disclosure.

FIG. 25b is a schematic structural view of another main body stent of a vascular stent in accordance with a nineteenth embodiment of the present disclosure.

FIG. 25c is a schematic structural view of another main body stent of a vascular stent in accordance with a nineteenth embodiment of the present disclosure.

FIG. 25d is a schematic structural view of another main body stent of a vascular stent in accordance with a nineteenth embodiment of the present disclosure.

DETAILED DESCRIPTION

The technical solution in the embodiments of the present disclosure will be clearly and completely described with reference to the drawings in the embodiments of the present disclosure. Obviously, the described embodiments are only a part of the embodiments of the present disclosure, but not all of them. Based on the embodiments in the present disclosure, all other embodiments obtained by a person of ordinary skill in the art without creative labor belong to the protection scope of the present disclosure.

In addition, the descriptions of the following embodiments are with reference to additional illustrations to exemplify specific embodiments that the present disclosure can be implemented with. Directional terms mentioned in the present disclosure, such as "up", "down", "front", "rear", "left", "right", "inside", "outside", "side", etc., only refer to the direction of the attached drawings. Therefore, the terminology used is to better and more clearly explain and understand the present disclosure, not to indicate or imply that the device or element referred to must have a specific orientation or must have a specific oriental structure and operation, and therefore cannot be understood as a limitation on the present disclosure.

In the description of the present disclosure, the "proximal end" of the present disclosure refers to the end near the heart position, and the "distal end" refers to the end away from the heart position. The high and low described in the present disclosure are relative to the covering of the main body tube. The end face exceeding the covering of the main body tube is called high, and the end face that does not exceed the covering of the main body tube is called low. The definition is only for convenience in expression and cannot be understood as a limitation on the present disclosure.

Figure 1:
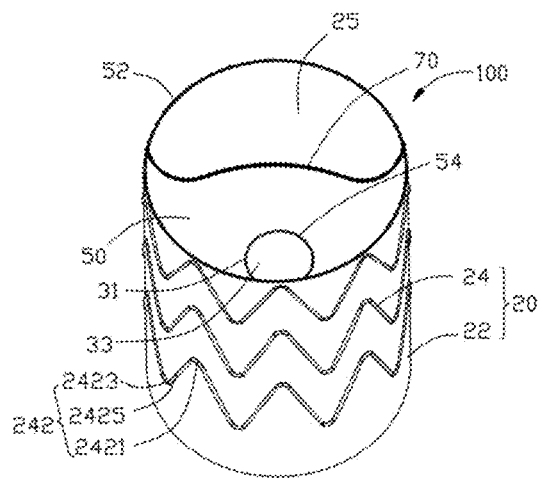
FIG. 1 is a schematic perspective view of a vascular shunt frame in accordance with a first embodiment of the present disclosure.
Figure 2:
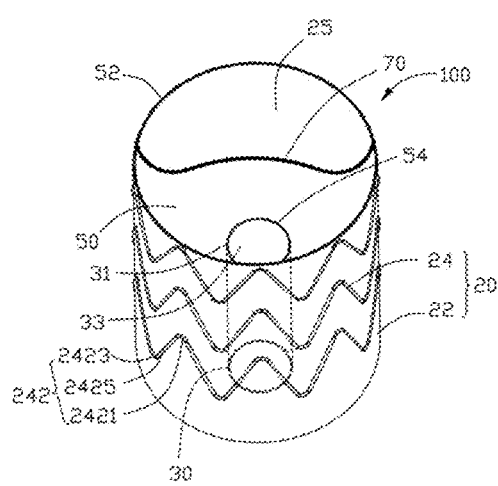
FIG. 2 is a schematic perspective view of a vascular shunt frame provided with a secondary body tube in accordance with a first embodiment of the present disclosure.
Figure 3:
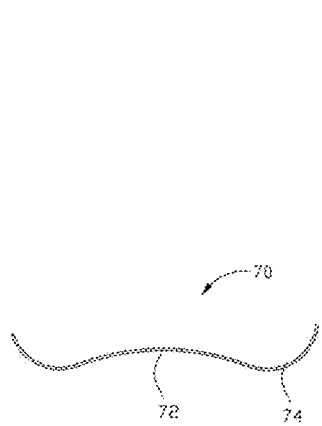
FIG. 3 is a schematic structural view of a shaping component of a vascular shunt frame in accordance with a first embodiment of the present disclosure.

Referring to FIGS. 1-3, FIG. 1 is a schematic perspective view of a vascular shunt frame in accordance with a first embodiment of the present disclosure. FIG. 2 is a schematic perspective view of a vascular shunt frame provided with a secondary body tube in accordance with a first embodiment of the present disclosure. FIG. 3 is a schematic structural view of a shaping component of a vascular shunt frame in accordance with a first embodiment of the present disclosure. The present disclosure provides a vascular shunt frame 100, which includes a main body tube 20. At least one end of the main body tube 20 is provided with a sealing covering 50; the sealing covering 50 is provided with a main blood flow opening 52, and an edge of the main blood flow opening 52 is provided with a shaping component.

In this embodiment, the shaping component is disposed on the sealing covering 50 on an edge of the main blood flow opening 52 away from a side of a side wall of the main body tube 20. The shaping component is a positioning rod 70 fixed to the sealing covering 50 on the main blood flow opening 52 away from a side of a side wall of the main body tube 20. The positioning rod 70 is used for positioning the sealing covering 50, that is, fixing the direction of the sealing covering 50, and increasing the supporting force of the opening edge of the sealing covering. The positioning rod 70 is made of a memory alloy wire, preferably a nickel-titanium alloy wire. The distal end of the main body tube 20 is provided with the sealing covering 50, i.e., one end of the main body tube 20 farther away from the heart is provided with the sealing covering 50. The sealing covering 50 is provided with the main blood flow opening 52. The positioning rod 70 extends along an edge of the main blood flow opening 52 connected with a side of a side wall of the main body tube 20 on the sealing covering 50 towards a center of the main body tube 20; two opposite ends of the positioning rod 70 are respectively connected to the side wall of the main body tube 20.

The vascular shunt frame 100 provided by the present disclosure, by disposing a shaping component on the edge of the sealing covering 50 of the main blood flow opening 54 away from a side of a side wall of the main body tube, locates the sealing covering 50. Therefore, when the main body stent is inserted into the main blood flow opening 52 of the main body tube 20, the shaping component can be closely attached to the outer surface of the main body stent, such that the sealing covering 50 is closely attached to the outer surface of the main body stent, to prevent endoleaks and make it convenient for the main body stent to be inserted into the main blood flow opening 52 of the main body tube 20, thereby increasing the compatibility between the main body stent and the shunt and making the joint between the main body stent and the shunt more stable.

As shown in FIG. 2, at least one secondary blood flow opening 54 is disposed on the sealing covering 50; at least one secondary body tube 30 is disposed in the main body tube 20; at least one of the secondary body tubes 30 is connected to at least one of the secondary blood flow openings 54. That is, the secondary body tube 30 is connected with the secondary blood flow opening 54. The secondary body tube 30 is formed by tubular partition coverings 31 independently, or formed by the enclosure of semi-tubular partition coverings 31 and the main body tube's tube wall 22. A shaping component may be disposed at an edge of at least one secondary blood flow opening 54 of the sealing covering 50, and the shaping component is an annular positioning rod 70 corresponding to the secondary blood flow opening 54. When a branch stent is inserted into the secondary blood flow opening 54, the positioning rod 70 at the edge of at least one secondary blood flow opening 54 can fix the branch stent in the secondary body tube 30, i.e., the positioning rod 70 can make the sealing covering 50 in a sealing contact with the outer surface of the branch stent to prevent endoleaks. In addition, the secondary body tube 30 can extend an anchoring area at the proximal end of the branch stent, further limits the branch stent, and increases the stability of the branch stent after releasing. The axial length of the secondary body tube 30 may be less than, greater than or equal to the axial length of the main body tube 20. In a case where multiple secondary body tubes 30 are disposed in the same vascular shunt frame 100, the sealing covering 50 may be provided with the shaping component on the edge of each secondary body tube 30, and the lengths of the secondary body tubes 30 may be the same or different.

In other embodiments, the sealing covering 50 is disposed on the proximal end of the main body tube 20, i.e., the sealing covering 50 is disposed on an end of the main body tube 20 closer to the heart. The sealing covering 50 is provided with at least one of the secondary blood flow openings 54 and the main blood flow opening 52, and a proximal end of the secondary body tube 30 is connected with the secondary blood flow opening 54. The positioning rod 70 is disposed on the edge of the sealing covering 50 adjacent to a side of the main blood flow opening 52, and two opposite ends of the positioning rod 70 are respectively connected to the proximal end of the main body tube 20; a positioning rod 70 is disposed on an edge of at least one of the secondary blood flow openings 54.

In other embodiments, the distal end and the proximal end of the main body tube 20 are provided with the sealing covering 50; each of the sealing coverings 50 is provided with a main blood flow opening 52 and at least one secondary blood flow opening 54; at least one of the secondary body tubes 30 is disposed in the main body tube 20; two ends of the secondary body tube 30 are respectively connected to the secondary blood flow openings 54 on two sealing coverings 50, i.e., the distal end of the secondary body tube 30 is connected to the secondary blood flow opening 54 on the sealing covering 50 at the distal end of the main body tube 20; the proximal end of the secondary body tube 30 is connected with the secondary blood flow opening 54 on the sealing covering 50 at the proximal end of the main body tube 20. The main blood flow openings 52 on the sealing coverings 50 at the proximal end and the distal end of the main body tube 20 are connected. The positioning rod 70 is disposed on an edge of each sealing covering 50 adjacent to a side of a corresponding main blood flow opening 52.

The positioning rod 70 extends along an edge of the sealing covering 50 adjacent to a side of the main blood flow opening 52, and two opposite ends of the positioning rod 70 are connected to the main body tube 20, respectively. Therefore, the positioning rod 70 may be a linear rod, a wavy rod, a curved rod, or other shaped rods.

As shown in FIG. 3, in this embodiment, the positioning rod 70 is a wave-shaped structure composed of three connected circular arc rods; the positioning rod 70 includes a first circular arc rod 72 located in the middle, and two second circular arc rods 74 connected to two opposite ends of the first circular arc rod 72; the two second circular arc rods 74 have the same structure and are symmetrical along a middle point of the first circular arc rod 72. The two second circular arc rods 74 and the first circular arc rod 72 are smoothly connected. The first circular arc rod 72 and the two second circular arc rods 74 are an integrated structure, and the positioning rod 70 is formed by bending and shaping a memory alloy wire.

In other embodiments, the first circular arc rod 72 and the two second circular arc rods 74 may be in a split structure, that is, the first circular arc rod 72 and the two second circular arc rods 74 are connected together by mechanically pressing or welding.

As shown in FIG. 1 and FIG. 2, a middle portion of the first circular arc rod 72 is bent toward the main blood flow opening 52, and a middle portion of each of the second circular arc rods 74 is bent toward a side away from the main blood flow opening 52, i.e., a middle portion of each of the second circular arc rods 74 is bent toward a side of the secondary blood flow opening 54.

The diameter of the positioning rod 70 is between 0.10-0.40 mm. In this embodiment, the diameter of the positioning rod 70 is 0.20-0.30 mm.

The main body tube 20 includes a tubular main body covering 22 and a main body tube support frame 24 fixed to a wall surface of the main body covering 22. The secondary body tube 30 is enclosed by a tubular partition covering 31, such that the inner cavity of the main body tube 20 is divided into a main body tube inner cavity 25 and a secondary body tube inner cavity 33. The distal end of the main body tube inner cavity 25 is connected with the main blood flow opening 52, and the distal end of the secondary body tube inner cavity 33 is connected with the secondary blood flow opening 54. The main body tube 20 is a main structure of the vascular shunt frame 100, and a shape of a transversal end face of the main body tube 20 is a circle or an ellipse that cooperates with a blood vessel. The main body tube support frame 24 is stitched on the main body covering 22, and the main body tube support frame 24 is formed by a plurality of annular wave-shaped supporting rods 242 arranged along the axial direction of the main body covering 22. Each annular wave-shaped supporting rod 242 may be a high wave supporting rod or a high-low wave supporting rod. The high wave supporting rod refers to that the heights of the peaks on the annular wave-shaped supporting rod 242 are the same, and the heights of the valleys are also the same, i.e., the peaks and the valleys are on the same plane, respectively; the high-low wave supporting rod refers to that the heights of the peaks on the annular wave-shaped supporting rod 242 are different, and the heights of the valleys may also be different.

The main body tube support frame 24 includes a plurality of sinusoidal wave-shaped supporting rods 242. These annular wave-shaped supporting rods 242 are arranged at intervals along the axial direction of the main body covering 22. Each sinusoidal waveform of each of the annular wave-shaped supporting rods 242 includes a peak 2421, a valley 2423, and a connecting rod 2425 connected between the peak 2421 and the valley 2423. Each annular wave-shaped supporting rod 242 is woven by a super-elastic nickel-titanium wire. The super-elastic nickel-titanium alloy wire has a selectable wire diameter (i.e., a diameter) ranging from 0.1 mm to 0.6 mm. A connection sleeve is disposed on each of the annular wave-shaped supporting rods 242, and the connection sleeve connects two opposite ends of the annular wave-shaped supporting rod 242, i.e., the two opposite ends of the annular wave-shaped supporting rod 242 are both received in the connection sleeve, then the two ends of the nickel-titanium wire are fixed inside the connection sleeve by mechanical pressing or welding.

In this embodiment, the annular wave-shaped supporting rod 242 is woven by using a nickel-titanium wire with a diameter of 0.5 mm; the number of the sinusoidal waves is nine; and the vertical height of the annular wave-shaped supporting rod 242 is 6-15 mm.

In other embodiments, the number of the sinusoidal waves may be other numbers, and the vertical height of the annular wave-shaped supporting rod 242 may be any value.

In other embodiments, the main body tube support frame 24 may be a woven mesh structure or a mesh structure formed by cutting.

The main body covering 22 is made of polyester cloth, PTFE, PET or other polymer materials, and the main body tube support frame 24 is stitched to the main body covering 22 by a suture, i.e., the suture can follow the wave trend of each of the annular wave-shaped supporting rods 242 and accompanies the entire main body tube support frame 24. The suture can also stitch each of the annular wave-shaped supporting rods 242 to the main body covering 22 by several non-equally spaced suture knots. The diameter of the suture is selected from a range of 0.05 mm-0.25 mm. Alternatively, the main body tube support frame 24 is fixedly connected to the main body covering 22 by hot pressing.

As shown in FIG. 2, the secondary body tube inner cavity 33 is enclosed by the partition covering 31 independently, and the empty cavity between the partition covering 31 and the main body covering 22 is the main body tube inner cavity 25. With this design, when the vascular shunt frame 100 is crimped, the overall diameter of the vascular shunt frame 100 can be reduced, thereby reducing the diameter of the delivery system used to assemble the sheath, and facilitating the delivery of the vascular shunt frame 100. The diameter of the main body tube inner cavity 25 is larger than the diameter of the secondary body tube inner cavity 33, and the number of the secondary body tubes 30 can be set according to actual needs, generally one to four, preferably one to three; the sealing covering 50 is provided with one to four secondary blood flow openings 54 corresponding to the secondary body tube 30, preferably two to four secondary blood flow openings 54. The shapes of the transverse end faces of the main body tube inner cavity 25 and the secondary body tube inner cavity 33 are circular, elliptical, fusiform, or irregularly curved.

In this embodiment, the number of the secondary body tubes 30 is one; the secondary body tube 30 contacts the inner surface of the main body tube 20; and the distal end of the secondary body tube 30 is connected with the secondary blood flow opening 54. The secondary blood flow opening 54 faces a middle point of the edge of the blood flow opening 54 adjacent to the main blood flow opening 52. The vascular shunt frame 100 includes a circular main body tube inner cavity 25 and a circular secondary body tube inner cavity 33.

The sealing covering 50 is disposed at a distal end of the main body tube 20, and the sealing covering 50 is in a sealed connection with the main body covering 22; the main blood flow opening 52 and the secondary blood flow opening 54 are both disposed on the sealing covering 50; the distal end of the partition covering 31 corresponds to the secondary blood flow opening 54 and is in a sealed connection to the sealing covering 50. That is, the sealing covering 50 connects the main body covering 22 and the partition covering 31 together, and closes a gap between the main body tube 20 and the secondary body tube 30. The opening area of the main blood flow opening 52 is smaller than the radial cross-sectional area of the main body covering 22, and the opening area of the secondary blood flow opening 54 is smaller than the opening area of the main blood flow opening 52.

In other embodiments, the opening area of the main blood flow opening 52 may be the same as the opening area of the secondary blood flow opening 54.

The sealing covering 50 may be disposed along the radial direction or an approximated radial direction of the main body tube 20.

In this embodiment, the sealing covering 50 is located at a distal end of the main body tube 20, and is stitched together with the main body covering 22 and the partition covering 31 by suturing. The end face of the distal end of the secondary blood flow opening 54 is lower than the end face of distal end of the main blood flow opening 52, i.e., the sealing covering 50 is recessed toward the secondary blood flow opening 54 such that the sealing covering 50 and the side wall of the main body tube 20 form a bell mouth opening, i.e., the sealing covering 50 is inclined toward the secondary blood flow opening 54. The sealing covering 50 is an inclined surface connecting the main blood flow opening 52, the secondary blood flow opening 54, the main body covering 22, and the partition covering 31. An angle between the inclined surface and the central axis of the main body tube 20 is 5-80 degrees, preferably 15-60 degrees.

In other embodiments, the sealing covering 50 may be a plane parallel to a radial direction of the main body tube 20, i.e., the sealing covering 50 is a plane perpendicular to a central axis of the main body tube 20.

The positioning rod 70 may be fixed on the sealing covering 50 by stitching or hot pressing. In this embodiment, the positioning rod 70 is fixed on the edge of the sealing covering 50 by stitching.

Figure 4:
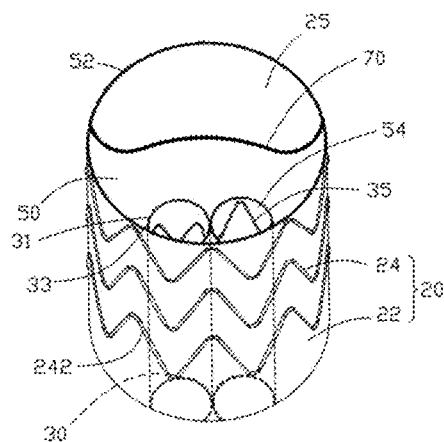
FIG. 4 is a schematic perspective view of a vascular shunt frame in accordance with a second embodiment of the present disclosure.

Referring to FIG. 4, FIG. 4 is a schematic perspective view of a vascular shunt frame in accordance with a second embodiment of the present disclosure. The structure of the vascular shunt frame provided in the second embodiment of the present disclosure is similar to that of the first embodiment, and the differences are: in the second embodiment, the sealing covering 50 is provided with two secondary blood flow openings 54; the main body tube inner chamber 20 of the main body tube 20 is provided with two secondary body tubes 30; the distal ends of the two secondary body tubes 30 are connected with the two secondary blood flow openings 54 respectively. The two secondary blood flow openings 54 are located on a side away from the main blood flow opening 54; and the outer sides of the two secondary body tubes 30 are in contact with the inner wall of the main body tube inner cavity 25. The end faces of the distal ends of the two secondary blood flow openings 54 are lower than the end face of the distal end of the main blood flow opening 52, such that the sealing covering 50 and the side wall of the main body tube 20 form a bell mouth opening.

A wave-shaped supporting rod 35 is fixed on the partition covering 31 of each secondary body tube 30. The wave-shaped supporting rod 35 can increase the supporting strength of the secondary body tube 30 and prevent the connected branch stent from being compressed by the main body stent to result in poor blood flow or even a blockage. The wave-shaped supporting rod 35 can be set according to the shape of the partition covering 31. That is, a wave-shaped supporting rod 35 may be fixed on the partition covering 31, or a plurality of wave-shaped supporting rods 35 may be arranged at intervals on the partition covering 31 along the axial direction, and the wave-shaped supporting rod 35 enclose to form the secondary body tube support frame of the partition covering 31. The wave-shaped supporting rod 35 may be annular or open-loop. The structure, shape, and material of the wave-shaped supporting rod 35 are similar to the annular wave-shaped supporting rod 242 on the main body tube 20, and details are not described herein again.

In other embodiments, three or more secondary blood flow openings 54 may be disposed on the sealing covering 50; three or more secondary body tubes 30 are disposed in a main body tube inner cavity 25 of the main body tube 20; each secondary blood flow opening 54 is connected with a corresponding secondary body tube 30.

In other embodiments, a woven mesh secondary body tube support frame may be fixed on the partition covering 31.

In other embodiments, the partition covering 31 may also be a semi-tubular structure. The partition covering 31 of the semi-tubular structure is stitched on the inner surface of the main body covering 22 to form a semi-circular secondary body tube together with the main body covering 22.

In another embodiment, a side of the main body covering 22 away from the secondary blood flow opening 54 may be cut into a V-shape or a U-shape. An edge of the main body covering 22 adjacent to the main body tube inner cavity 25 is provided with a V-shaped or U-shaped positioning rod 70. When the main body tube 22 is used with a branch vascular stent or other branch stent, the visibility around the secondary body tube 30 can be increased, and the branch vascular stent can be more easily inserted. The above structure may be provided at the distal end of the main body tube 22, or at the proximal end of the main body tube 22, or at both the distal end and the proximal end of the main body tube 22.

Figure 5:
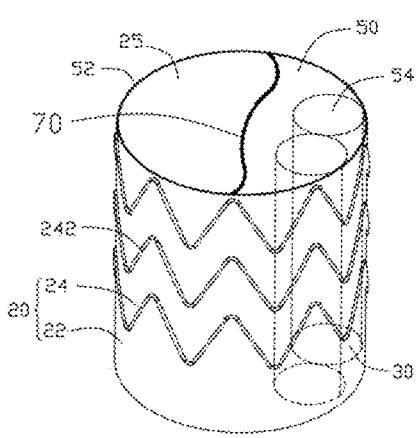
FIG. 5 is a schematic perspective view of a vascular shunt frame in accordance with a third embodiment of the present disclosure.

Referring to FIG. 5, FIG. 5 is a schematic perspective view of a vascular shunt frame in accordance with a third embodiment of the present disclosure. The structure of the vascular shunt frame provided in the third embodiment of the present disclosure is similar to that of the second embodiment, and the differences are: in the third embodiment, the sealing covering 50 is parallel to a plane of the radial direction of the main body tube 20, i.e., the sealing covering 50 is perpendicular to a plane of the central axis of the main body tube 20.

Figure 6:
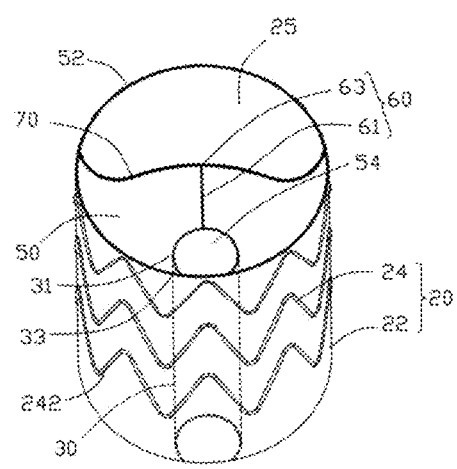
FIG. 6 is a schematic perspective view of a vascular shunt frame in accordance with a fourth embodiment of the present disclosure.

Referring to FIG. 6, FIG. 6 is a schematic perspective view of a vascular shunt frame in accordance with a fourth embodiment of the present disclosure. The structure of the vascular shunt frame provided by the fourth embodiment of the present disclosure is similar to that of the first embodiment, and the differences are: in the fourth embodiment, at least one supporting rod 60 is disposed on the sealing covering 50; one end of the supporting rod 60 is connected to the positioning rod 70; the other end of the supporting rod 60 is connected to an edge of the secondary blood flow opening 54 adjacent to the main blood flow opening 52. Both the supporting rod 60 and the positioning rod 70 can support the sealing covering 50, to allow the sealing covering 50 to fully spread, and make the sealing covering 50 extend in a direction away from the main blood flow opening 52, to prevent the sealing covering 50 from bending and moving toward the main blood flow opening 52 or the secondary blood flow opening 54 to obstruct the main blood flow opening 52 or the secondary blood flow opening 54; when a main body stent is fitted and connected with the main blood flow opening 52, the positioning rod 70 can be closely attached to the outer surface of the main body stent, and the sealing covering 50 is brought into close contact with the outer surface of the main body stent to prevent blood endoleaks in the main body tube 20.

The supporting rod 60 includes a rod body 61 and two suturing rings 63 disposed at both ends of the rod body 61. One of the suturing rings 63 is connected to the positioning rod 70, and the other of the suturing rings 63 is connected to the edge of the secondary blood flow opening 54. The material of the supporting rod 60 is a nickel-titanium wire with a wire diameter of 0.10-0.40 mm, and preferably a wire diameter of 0.20-0.30 mm.

In this embodiment, one of the suturing rings 63 of the supporting rod 60 is fixed to the first circular arc rod 72 of the positioning rod 70, and the other of the suturing rings 63 of the supporting rod 60 is fixed to the edge of the secondary blood flow opening 54 adjacent to the positioning rod 70. Preferably, one of the suturing rings 63 of the supporting rod 60 is fixed to a middle point of the first circular arc rod 72.

The supporting rod 60 is fixed on the sealing covering 50 of the vascular shunt frame 100 of the present disclosure between the positioning rod 70 and the edge of the secondary blood flow opening 54. The supporting rod 60 can fix the direction of the sealing covering 50 such that the sealing covering 50 extends forward, instead of bending or inclining towards the secondary blood flow opening 54 or the main blood flow opening 52, i.e., the sealing covering 50 can be completely spread out without folding such that it does not interfere with the secondary blood flow opening 54 or the main blood flow opening 52, thereby preventing the sealing covering 50 from blocking the secondary blood flow opening 54 or the main blood flow opening 52; the supporting rod 60 can also provide guidance for the branch vascular stent inserted on the secondary blood flow opening 54 of the vascular shunt frame 100, i.e., the traction guide wire of the branch vascular stent may slide into the secondary blood flow opening 54 along the smooth sealing covering 50, making it convenient for inserting the branch vascular stent and improving the work efficiency.

Figure 7:
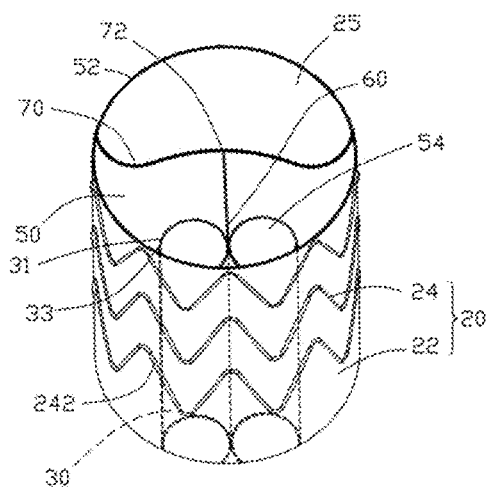
FIG. 7 is a schematic perspective view of a vascular shunt frame in accordance with a fifth embodiment of the present disclosure.

Referring to FIG. 7, FIG. 7 is a schematic perspective view of a vascular shunt frame in accordance with a fifth embodiment of the present disclosure. The structure of the vascular shunt frame provided by the fifth embodiment is similar to that of the fourth embodiment, and the differences are: in the fifth embodiment, the sealing covering 50 is provided with two tangential secondary blood flow openings 54; two secondary body tubes 30 are disposed in the main body tube inner cavity 25 of the main body tube 20; and two distal ends of the two secondary body tubes 30 are connected with the two secondary blood flow openings 54 respectively. The two secondary blood flow openings 54 are located on a side away from the main blood flow opening 54, and the outer sides of the two secondary body tubes 30 are attached to the inner wall of the main body tube inner cavity 25. The supporting rod 60 is fixed to the sealing covering 50, and is connected between the positioning rod 70 and a tangential point of the two secondary blood flow openings 54. The sealing covering 50 is recessed toward the two secondary blood flow openings 54, i.e., the sealing covering 50 is inclined toward the two secondary blood flow openings 54.

In this embodiment, one end of the supporting rod 60 is fixed to the first circular arc rod 72 of the positioning rod 70, and is preferably fixed to a middle point of the first circular arc rod 72. The other end of the supporting rod 60 is fixed to between the tangential point of the secondary blood flow openings 54.

Figure 8:
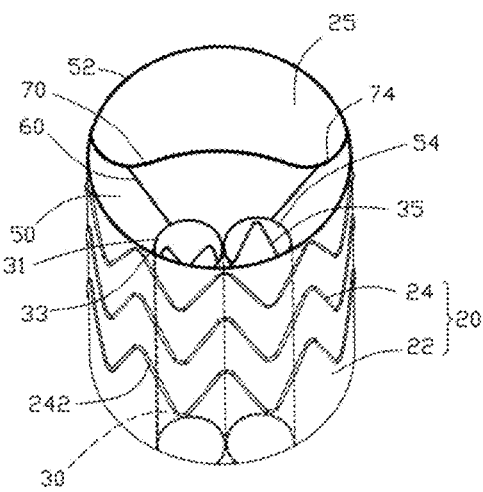
FIG. 8 is a schematic perspective view of a vascular shunt frame in accordance with a sixth embodiment of the present disclosure.

Referring to FIG. 8, FIG. 8 is a schematic perspective view of a vascular shunt frame in accordance with a sixth embodiment of the present disclosure. The structure of the vascular shunt frame provided by the sixth embodiment of the present disclosure is similar to that of the fifth embodiment, and the differences are: in the sixth embodiment, two sealing blood flow openings 54 are disposed on the sealing covering 50. Two sealing rods 60 are fixed to the sealing covering 50 at intervals; the two supporting rods 60 are respectively connected between the edges of the two secondary blood flow openings 54 and the positioning rod 70. Specifically, one end of each supporting rod 60 is fixed on the second circular arc rod 74 of the positioning rod 70, and the other end is fixed on the edge of the corresponding secondary blood flow opening 54.

In this embodiment, the two supporting rods 60 have a shape of an inverted figure eight expressed in Simplified Chinese.

In other embodiments, two supporting rods 60 may be fixed to the sealing covering 50 in parallel with each other, and each supporting rod 60 is connected between an edge of a corresponding secondary blood flow opening 54 and the positioning rod 70.

Figure 9:
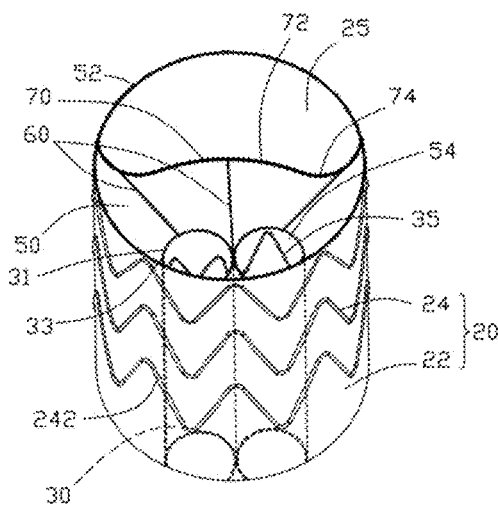
FIG. 9 is a schematic perspective view of a vascular shunt frame in accordance with a seventh embodiment of the present disclosure.

Referring to FIG. 9, FIG. 9 is a schematic perspective view of a vascular shunt frame in accordance with a seventh embodiment of the present disclosure. The structure of the vascular shunt frame provided by the seventh embodiment is similar to that of the sixth embodiment, and the differences are: the seventh embodiment adds a supporting rod 60 to the sixth embodiment, that is, three supporting rods 60 are fixed on the sealing covering 50; the three supporting rods 60 are arranged at intervals; one supporting rod 60 in the middle is connected between the tangent point of the two secondary blood flow openings 54 and the first circular arc rod 72 of the positioning rod 70; two supporting rods 60 on both sides are respectively connected between the edges of two secondary blood flow openings 54 and two second circular arc rods 74 of the positioning rod 70. By using both the three supporting rods 60 and the positioning rod 70 together to support the sealing covering 50, it can make the sealing covering 50 more stable and not be folded to interfere with or block the secondary blood flow opening 54 or the main blood flow opening 52, such that the blood flow inside the main body tube 20 and the secondary body tube 30 is more smooth, thereby making it convenient to insert the branch vascular stent.

In this embodiment, one end of the middle supporting rod 60 is connected to the tangential point of the two secondary blood flow openings 54, and the other end is connected to the middle point of the first circular arc rod 72; the two supporting rods 60 on both sides are arranged symmetrically, i.e., the two supporting rods 60 on both sides are symmetrical along a plane defined by the tangential point of the two secondary blood flow openings 54 and the central axis of the main body tube 20.

Figure 10:
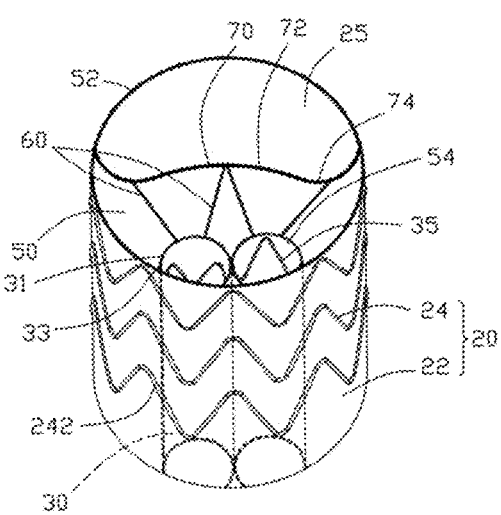
FIG. 10 is a schematic perspective view of a vascular shunt frame in accordance with an eighth embodiment of the present disclosure.

Referring to FIG. 10, FIG. 10 is a schematic perspective view of a vascular shunt frame in accordance with an eighth embodiment of the present disclosure. The structure of the vascular shunt frame provided by the eighth embodiment of the present disclosure is similar to that of the sixth embodiment, and the differences are: two supporting rods 60 are added to the sixth embodiment, that is, four supporting rods 50 are fixed to and spaced apart on the sealing covering 50; two out of the four supporting rods 60 are connected between the edge of one secondary blood flow opening 54 and the positioning rod 70; the other two out of the four supporting rods 60 are connected between the edge of the other secondary blood flow opening 54 and the positioning rod 70, i.e., the two supporting rods 60 in the middle are connected between the two secondary blood flow openings 54 and the first circular arc rod 72 of the positioning rod 70; the two supporting rods 60 on both sides are connected between the two secondary blood flow openings 54 and the two second circular arc rods 74 of the positioning rod 70. In this embodiment, by using the four supporting rods 60 and the positioning rod 70 together to support the sealing covering 50, it can make the sealing covering 50 more stable, and will not be folded to interfere with or block the secondary blood flow opening 54 or the main blood flow opening 52, such that the blood flow inside the main body tube 20 and the secondary body tube 30 is more smooth, thereby making it convenient to insert the main body stent or the branch vascular stent; and when the main body stent is inserted into the main blood flow opening 52, the positioning rod 70 can be closely attached to the outer surface of the branch vascular stent to prevent endoleaks.

In this embodiment, the four supporting rods 60 are symmetrical along the plane defined by the tangential point of the two secondary blood flow openings 54 and the central axis of the main body tube 20. The two supporting rods 60 in the middle are in an inverted "V" shape, and each supporting rod 60 is connected between the middle portion of the first circular arc rod 72 of the positioning rod 70 and the edge of the corresponding secondary blood flow opening 54; the two supporting rods on both sides have a shape of an inverted figure eight expressed in Simplified Chinese, and each supporting rod 60 is connected between the second circular arc rod 74 of the positioned rod 70 and the edge of the corresponding secondary blood flow opening 54.

In other embodiments, more than four supporting rods 60, such as five and six, may be fixed on the sealing covering 50. A part of the supporting rods 60 is connected to between the edge of one of the secondary blood flow openings 54 and the positioning rod 70; another part of the supporting rods 60 is connected between the edge of another of the secondary blood flow openings 54 and the positioning rod 70.

In other embodiments, the sealing covering 50 may be provided with a plurality of the secondary blood flow openings 54. The sealing covering 50 may be fixed with a plurality of supporting rods 60 corresponding to the plurality of the secondary blood flow openings 54. Each supporting rod 60 is connected to between an edge of a corresponding secondary blood flow opening 54 and the positioning rod 70.

In other embodiments, four supporting rods 60 may be disposed on the sealing covering 50 in parallel and spaced apart.

Figure 11:
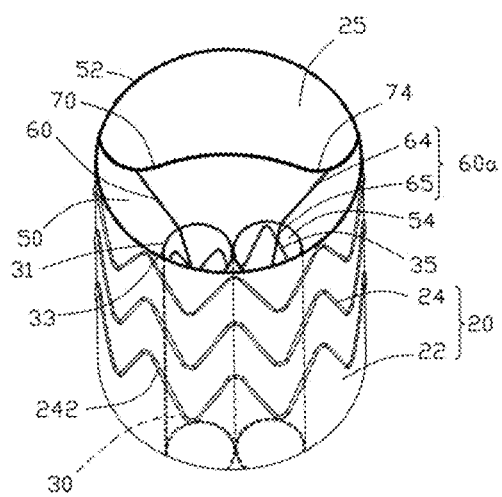
FIG. 11 is a schematic perspective view of a vascular shunt frame in accordance with a ninth embodiment of the present disclosure.
Figure 11A:
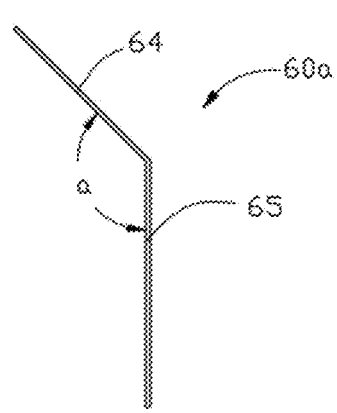
FIG. 11a is a schematic structural view of a supporting component of a vascular shunt frame in accordance with a ninth embodiment of the present disclosure.

Referring to FIG. 11 together, FIG. 11 is a schematic perspective of a vascular shunt frame in accordance with a ninth embodiment of the present disclosure. The structure of the vascular shunt frame provided by the ninth embodiment is similar to that of the sixth embodiment, and the differences are: the structure of the supporting rod 60a in the ninth embodiment is different from the structure of the supporting rod 60 in the sixth embodiment; as shown in FIG. 11a, the supporting rod 60a includes a first rod body 64 and a second rod body 65 inclinedly connected to one end of the first rod body 64. An angle between the first rod body 64 and the second rod body 65 ranges from 24 to 130 degrees. The first rod body 64 of each supporting rod 60a is fixed on the sealing covering 50, and the second rod body 65 is fixed on the side wall of the corresponding secondary body tube 30, i.e., the second rod body 65 is fixed on the partition covering 31 of the corresponding secondary body tube 30; the intersection of the first rod body 64 and the second rod body 65 is located at the intersection of the sealing covering 50 and the side wall of the corresponding secondary body tube 30. The inclination angle of the first rod body 64 is the same as that of the sealing covering 50, and the second rod body 65 extends along the axial direction of the corresponding partition covering 31. An end of each first rod body 64 away from the corresponding second rod body 65 is fixed on the positioning rod 70. Preferably, an end of each first rod body 64 away from the corresponding second rod body 65 is fixed on the corresponding second circular arc rod 74.

In this embodiment, the first rod body 64 and the second rod body 65 are integrated, and the angle between the first rod body 64 and the second rod body 65 is formed by hot pressing and bending. The first rod body 64 and the second rod body 65 are respectively fixed on the sealing covering 50 and the partition covering 31 by stitching.

The first rod body 64 of the supporting rod 60a in this embodiment is fixed on the sealing covering 50, and the end of the first rod body 64 away from the second rod body 65 is fixed on the positioning rod 70. The supporting rod 60a and the positioning rod 70 have a supporting effect on the sealing covering 50; the second rod body 65 is fixed on the partition covering 31, which can not only support the sealing covering 50, but also locate the corresponding partition covering 31, thereby enhancing the radial supporting force of the secondary body tube 30, and making the sealing covering 50 and the side wall of the main body tube 20 to enclose to form a stable bell mouth opening structure, such that the blood flow in the main body tube 20 and the secondary body tube 30 is more smooth, and it is convenient to insert the branch vascular stent into the main blood flow opening 52 and the secondary blood flow opening 54.

In other embodiments, the first rod body 64 and the second rod body 65 may also be a split design, and the connection points of the first rod body 64 and the second rod body 65 are combined by welding, or the first rod body 64 and the second rod body 65 are abutted, and then fixed to the sealing covering 50 and the partition covering 31, respectively.

In other embodiments, the sealing covering 50 may be provided with only one supporting rod 60a. The first rod body 64 of the supporting rod 60a is fixed on the sealing covering 50; the end of the first rod body 64 away from the second rod body 65 is fixed on the positioning rod 70; the second rod body 65 is fixed on the tangential point of the two secondary body tubes 30.

In other embodiments, the sealing covering 50 may be provided with only one supporting rod 60a; the sealing covering 50 may be provided with only one secondary blood flow opening 54; the first rod body 64 of the supporting rod 60a may be fixed on the sealing covering 50; the second rod body 65 is fixed on the partition covering 31 of the secondary blood flow opening 54; the intersection of the first rod body 64 and the second rod body 65 is located at the intersection of the sealing covering 50 and the partition covering 31; the first rod body 64 is away from one end of the second rod body 65 and is connected to the positioning rod 70.

Figure 12:
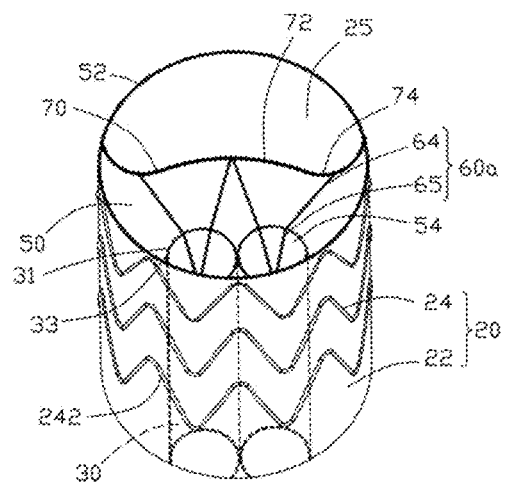
FIG. 12 is a schematic perspective view of a vascular shunt frame in accordance with a tenth embodiment of the present disclosure.
Figure 13:
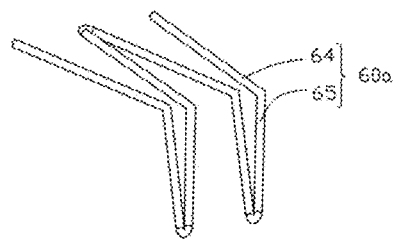
FIG. 13 is a schematic structural view of a supporting component of a vascular shunt frame in accordance with a tenth embodiment of the present disclosure.

Referring to FIG. 12 and FIG. 13 together, FIG. 11 is a schematic perspective view of a vascular shunt frame in accordance with a tenth embodiment of the present disclosure. FIG. 12 is a schematic structural view of a supporting component of the vascular shunt frame in accordance with the tenth embodiment of the present disclosure. The structure of the vascular shunt frame provided by the tenth embodiment of the present disclosure is similar to that of the ninth embodiment, and the differences are: in the tenth embodiment, four supporting rods 60a are disposed on the sealing covering 50; the four supporting rods 60a are connected end to end to enclose and form a supporting component in a "W" shape; the middle portion of the "W" shaped supporting component is folded toward the same side. The first rod body 64 of each supporting rod 60*a* is fixed to the sealing covering 50; the second rod body 65 of the supporting rod 60*a* is fixed to the partition covering 31 of the corresponding secondary body tube 30; the intersection of the first rod body 64 and the second rod body 65 is located at the intersection of the sealing covering 50 and the corresponding partition covering 31. An end of each first rod body 64 away from the corresponding second rod body 65 is fixed on the positioning rod 70.

In this embodiment, the four supporting rods 60*a* are in an integral symmetrical structure, and the connection points between the first rod bodies 64 of the two supporting rods 60*a* in the middle are connected to the middle portion of the first circular arc rod 72 of the positioning rod 70; the two second rod bodies 65 are respectively fixed on the partition coverings 31 of the two secondary body tubes 30, such that the two supporting rods 60*a* in the middle form an inverted "V" shape structure. The first rod bodies 64 of the two supporting rods 60*a* on both sides are respectively connected between the edge of the corresponding secondary blood flow opening 54 and the two circular arc rods 74 of the positioning rod 70; the bottom ends of the two second rod bodies 65 are respectively connected to the bottom ends of the second rod bodies 65 of the two supporting rods 60*a* in the middle, and are fixed to the partition covering 31 of the corresponding secondary body tube 30, i.e., the two second rod bodies 65 on the partition covering 31 of each secondary body tube 30 enclose to form a "V" shape structure.

In this embodiment, the first rod bodies 64 of the four supporting rods 60*a* are fixed to the sealing covering 50 at intervals, and are all connected to the positioning rod 70, thereby having a better support for the sealing covering 50. The second rod bodies 65 of the four supporting rods 60*a* enclose to form two "V" shape support structures, and are respectively fixed to the partition covering 31 of the two secondary body tubes 30, thereby further enhancing the radial supporting force of the secondary body tube 30, such that the sealing covering 50 and the side wall of the main body tube 20 enclose to form a more stable bell mouth opening structure, making the blood flow in the main body tube 20 and the secondary body tube 30 more smooth, and making it convenient to insert the branch vascular stent.

Figure 14:
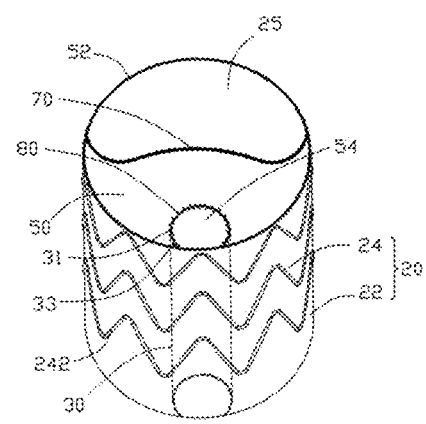
FIG. 14 is a schematic perspective view of a vascular shunt frame in accordance with an eleventh embodiment of the present disclosure.
Figure 15:
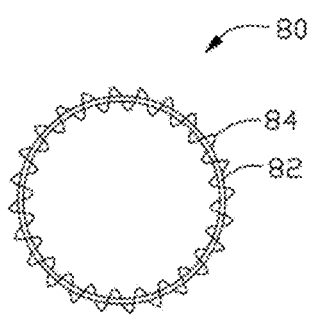
FIG. 15 is a schematic structural view of a radiopaque structure of a vascular shunt frame in accordance with an eleventh embodiment of the present disclosure.

Referring to FIG. 14 and FIG. 15 together, FIG. 14 is a schematic perspective view of a vascular shunt frame in accordance with an eleventh embodiment of the present disclosure. FIG. 15 is a schematic structural view of a radiopaque structure of a vascular shunt frame provided by the eleventh embodiment of the present disclosure. The structure of the vascular shunt frame provided in the eleventh embodiment of the present disclosure is similar to that of the first embodiment, and the differences are: in the eleventh embodiment, the secondary body tube 30 is provided with a radiopaque structure 80 at the edge of the secondary blood flow opening 54. The radiopaque structure 80 includes a supporting component 82 and a radiopaque component 84. The supporting component 82 is a metal ring or metal rod adapted to the shape of the edge of the secondary blood flow opening 54; the radiopaque component 84 is a radiopaque wire continuously or intermittently wound on the metal ring or metal rod. Or the supporting component 82 of the radiopaque structure 80 is made of an alloy doped with a radiopaque material, for example, the nickel-titanium alloy wire made by a nickel-titanium alloy wire containing tantalum; and the diameter of the nickel-titanium alloy wire 84 is 0.10-0.40 mm. Or the radiopaque structure 80 is a radiopaque ring.

In this embodiment, the supporting component 82 is a metal ring made of a memory alloy, such as a nickel-titanium alloy annular structure. The metal ring is adapted to the shape of the edge of the secondary blood flow opening 54. The radiopaque component 84 is a radiopaque wire continuous or discontinuous wound on the metal ring. Since the annular radiopaque structure 80 has a radiopaque property and is an annular structure, the position of the annular radiopaque structure 80 can be clearly observed by an imaging device during surgery, that is, the annular radiopaque structure 80 can be observed as a circle of the edge of the secondary blood flow 54 rather than scattered radiopaque markers. Therefore, it is more convenient and quick to insert a branch vascular stent in the secondary blood flow opening 54. The material for the radiopaque component includes, but is not limited to, gold, platinum, platinum-tungsten, palladium, platinum-iridium, rhodium, tantalum, or alloys or composites of these metals.

In other embodiments, a least a circle of the radiopaque material may be inlaid or pasted on the outer surface of the supporting component 82, such as inlaying a radiopaque metal wire on the supporting component 82, or pasting at least a circle of radiopaque metal wire 84 on the outer surface of the supporting component 82. Preferably, a tantalum wire is wound on the supporting component.

In other embodiments, the annular radiopaque structure 80 are radiopaque markers continuously or intermittently fixed on the edge of the secondary blood flow opening 54 on the sealing covering 50, and the radiopaque markers are stitched, stamped, hot-pressed, mounted or attached to be fixed on the supporting component 82 or are stitched on the sealing covering 50 where the supporting component 82 is located.

In other embodiments, the edge of the main blood flow opening 52 is also provided with an annular radiopaque structure 80. The annular radiopaque structure 80 are radiopaque markers continuously or intermittently fixed on the sealing covering 50 on the edge of the main blood flow opening 52.

In other embodiments, the supporting component 82 is a metal ring or metal rod adapted to the shape of the edge of the main blood flow opening 52 or the secondary blood flow opening 54, and the radiopaque component 84 is a radiopaque wire continuously or intermittently wound on the metal ring or metal rod.

In other embodiments, the positioning rod 70 may be made of a memory alloy wire containing a radiopaque material to facilitate the insertion of a branch vascular stent in the main blood flow opening 52.

In other embodiments, the positioning rod 70 is continuously or intermittently wound with a radiopaque wire.

In other embodiments, a radiopaque structure is mounted on or attached to the positioning rod 70. For example, a radiopaque metal wire is mounted on the positioning rod 70.

In other embodiments, the distal end or the proximal end of the main body tube 20 may be provided with an annular radiopaque structure 80 at the edge of the main blood flow opening 52.

In other embodiments, at least a circle of a radiopaque wire, such as a tantalum, platinum, or palladium wire, can be mounted or attached on the outer surface of the supporting component 82. Preferably, a tantalum wire is wound on the supporting component 82.

In other embodiments, the proximal end of each secondary body tube 30 is also provided with an annular radiopaque structure 80 at the edge of the secondary blood flow opening 54.

In other embodiments, the distal end of the main body tube 20 may be provided with an annular radiopaque structure 80 at the edge of the main blood flow opening 52.

In other embodiments, the radiopaque component 84 is a radiopaque structure mounted on or attached to the outer surface of the metal ring or metal rod.

In other embodiments, the radiopaque component 84 is a radiopaque material fused in the supporting component 82, that is, the radiopaque component 84 is a radiopaque material fused in a metal ring or a metal rod. The supporting component 82 is formed by enclosing a tantalum-containing nickel-titanium alloy wire; the diameter of the wire of the supporting component 82 is 0.10-0.40 mm; and the outer diameter of the supporting component 82 is 12-16 mm. Because the supporting component 82 is made of an alloy containing a radiopaque material, the supporting component 82 can be directly used as a radiopaque structure, and there is no need to dispose the radiopaque component 84 on the supporting component 82. During the operation, the position of the supporting component 82 can be clearly observed by an imaging device, and a branch vascular stent can be conveniently and quickly inserted into the secondary blood flow opening 54, making it convenient to use.

In other embodiments, an annular radiopaque structure 80 is disposed at an edge at the position of the tube opening of the proximal end of the tube opening of the secondary body tube 30; the design of the annular radiopaque structure 80 is the same as the design of the annular radiopaque structure 80 at the edge of the secondary blood flow opening 54. By disposing a radiopaque structure at the edges of the tube opening of the proximal end and the tube opening of the distal end of the secondary body tube 30 (and corresponding secondary blood flow openings) of the secondary body tube 30, it is convenient for a surgery operator to more clearly find the path of the secondary body tube during the operation and it is convenient for the establishment of an access path of the guide wire guided by the branch vascular stent, thereby saving operation time and reducing the risk of surgery.

In other embodiments, the annular radiopaque structure 80 can also be disposed on the partition covering 31 of the secondary body tube 30. Preferably, a plurality of radiopaque markers are disposed continuous or intermittent on the partition covering 31 along the axial direction from the proximal end to the distal end, and are fixed on the partition covering 31 by suturing, stamping, hot pressing, mounting or attaching. The axially arranged radiopaque markers may be arranged at intervals of one to four in the circumferential direction. The axially arranged radiopaque markers can further mark the extension direction of the secondary body tube, so that the surgery operator can complete the operation more quickly during the operation.

Figure 16:
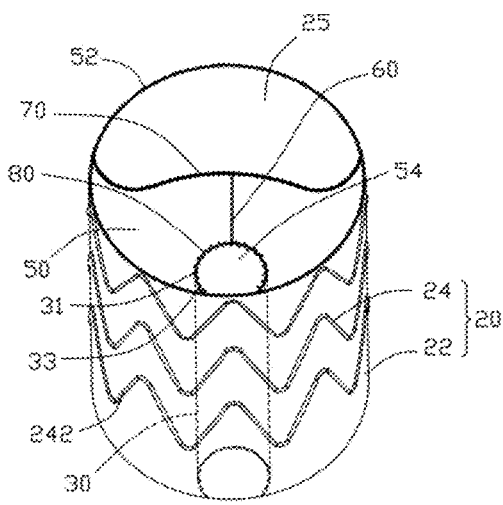
FIG. 16 is a schematic perspective view of a vascular shunt frame in accordance with a twelfth embodiment of the present disclosure.

Referring to FIG. 16, FIG. 16 is a schematic perspective view of a vascular shunt frame in accordance with a twelfth embodiment of the present disclosure. The structure of the vascular shunt frame provided in the twelfth embodiment of the present disclosure is similar to that of the fourth embodiment, and the differences are: in the twelfth embodiment, the distal end of the secondary body tube 30 is provided with above-mentioned annular radiopaque structure 80 around the secondary blood flow opening 54; further, the edge of the tube opening of the proximal end of the tube opening of the secondary body tube 30 is also provided with an annular radiopaque structure 80.

Figure 17:
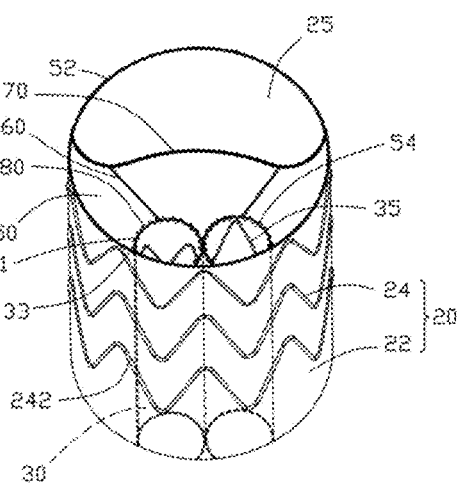
FIG. 17 is a schematic perspective view of a vascular shunt frame in accordance with a thirteenth embodiment of the present disclosure.

Referring to FIG. 17, FIG. 17 is a schematic perspective view of a vascular shunt frame in accordance with a thirteenth embodiment of the present disclosure. The structure of the vascular shunt frame provided in the thirteenth embodiment of the present disclosure is similar to that of the sixth embodiment, and the differences are: in the thirteenth embodiment, the distal end of each secondary body tube 30 is provided with the above-mentioned annular radiopaque structure 80 around the secondary blood flow opening 54; further, the edge of the tube opening of the proximal end of the tube opening of the secondary body tube 30 is also provided with an annular radiopaque structure 80.

Figure 18:
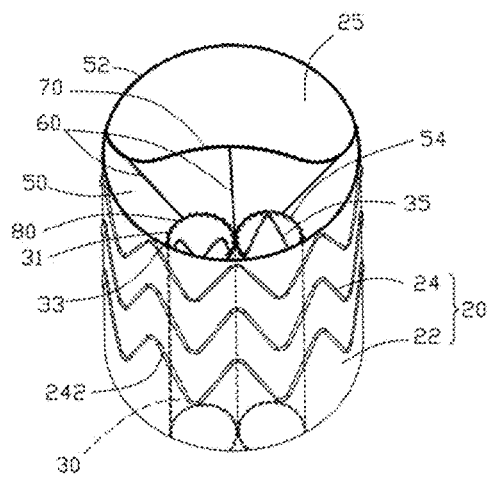
FIG. 18 is a schematic perspective view of a vascular shunt frame in accordance with a fourteenth embodiment of the present disclosure.

Referring to FIG. 18, FIG. 18 is a schematic perspective view of a vascular shunt frame in accordance with a fourteenth embodiment of the present disclosure. The structure of the vascular shunt frame provided by the fourteenth embodiment of the present disclosure is similar to that of the seventh embodiment, and the differences are: in the fourteenth embodiment, the distal end of each secondary body tube 30 is provided with the above-mentioned annular radiopaque structure 80 around the secondary blood flowing opening 54; further, the edge of the tube opening of the proximal end of the tube opening of the secondary body tube 30 is also provided with an annular radiopaque structure 80.

Figure 19:
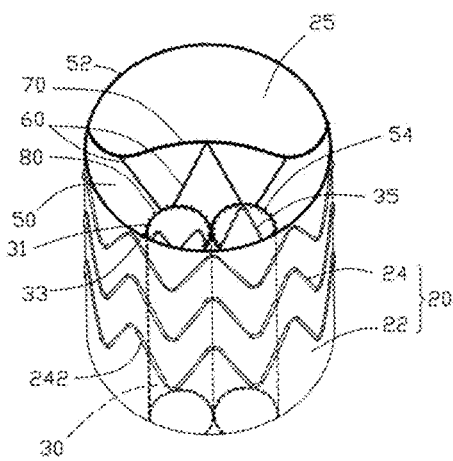
FIG. 19 is a schematic perspective view of a vascular shunt frame in accordance with a fifteenth embodiment of the present disclosure.

Referring to FIG. 19, FIG. 19 is a schematic perspective view of a vascular shunt frame in accordance with a fifteenth embodiment of the present disclosure. The structure of the vascular shunt frame provided by the fifteenth embodiment of the present disclosure is similar to that of the eighth embodiment, and the differences are: in the fifteenth embodiment, the distal end of each secondary body tube 30 is provided with the above-mentioned annular radiopaque structure 80 around the secondary blood flowing opening 54; further, the edge of the tube opening of the proximal end of the tube opening of the secondary body tube 30 is also provided with an annular radiopaque structure 80.

Figure 20:
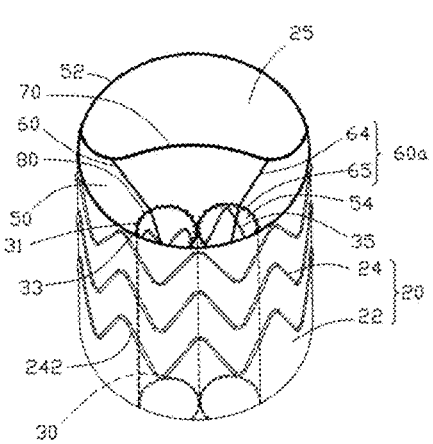
FIG. 20 is a schematic perspective view of a vascular shunt frame in accordance with a sixteenth embodiment of the present disclosure.

Referring to FIG. 20, FIG. 20 is a schematic perspective view of a vascular shunt frame in accordance with a sixteenth embodiment of the present disclosure. The structure of the vascular shunt frame provided by the sixteenth embodiment of the present disclosure is similar to that of the ninth embodiment, and the differences are: in the sixteenth embodiment, the distal end of each secondary body tube 30 is provided with the above-mentioned annular radiopaque structure 80 around the secondary blood flowing opening 54; further, the edge of the tube opening of the proximal end of the tube opening of the secondary body tube 30 is also provided with an annular radiopaque structure 80.

Figure 21:
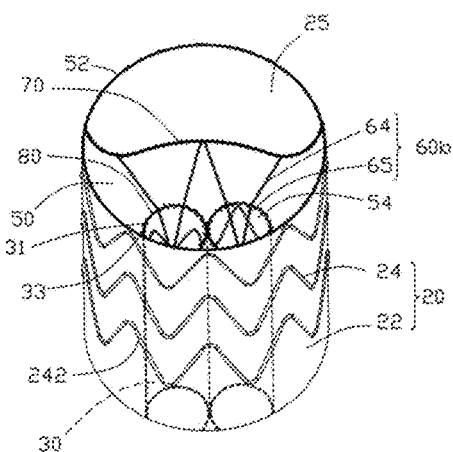
FIG. 21 is a schematic perspective view of a vascular shunt frame in accordance with a seventeenth embodiment of the present disclosure.

Referring to FIG. 21, FIG. 21 is a schematic perspective view of a vascular shunt frame in accordance with a seventeenth embodiment of the present disclosure. The structure of the vascular shunt frame provided by the seventeenth embodiment of the present disclosure is similar to that of the tenth embodiment, and the differences are: in the seventeenth embodiment, the distal end of each secondary body tube 30 is provided with the above-mentioned annular radiopaque structure 80 around the secondary blood flowing opening 54; further, the edge of the tube opening of the proximal end of the tube opening of the secondary body tube 30 is also provided with an annular radiopaque structure 80.

Figure 22:
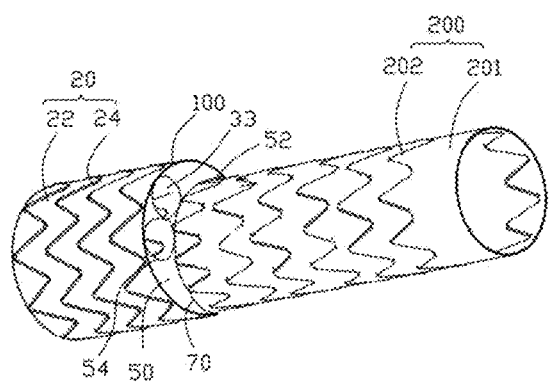
FIG. 22 is a schematic perspective view of a vascular stent in accordance with an eighteenth embodiment of the present disclosure.
Figure 23:
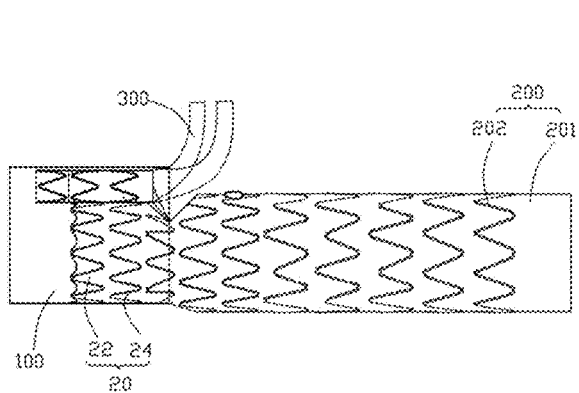
FIG. 23 is a schematic diagram of a vascular stent in one operating state in accordance with an eighteenth embodiment of the present disclosure.

Referring to FIG. 22 and FIG. 24 together, FIG. 22 is a schematic perspective view of the vascular stent in accordance with the eighteenth embodiment of the present disclosure. FIG. 23 is a schematic diagram of a vascular stent in one operating state in accordance with an eighteenth embodiment of the present disclosure. FIG. 24 is a schematic diagram of a vascular stent in another operating state in accordance with an eighteenth embodiment of the present disclosure. The present disclosure also provides a vascular stent, which includes a main body stent 200 and a vascular shunt frame 100. The vascular shunt frame 100 includes a main body tube 22. At least one end of the main body tube 22 is provided with a sealing covering 50; the sealing covering 50 is provided with a main blood flow opening 52; an edge of a side of the sealing covering 50 adjacent to the main blood flow opening 52 is provided with a shaping component 70; one end of the main body stent 200 passes through the main blood flow opening 52 on the sealing covering 50 and is inserted into the main body tube 20 of the vascular shunt frame 100; the positioning rod 70 is closely attached to the outer surface of the main body stent 200, such that the sealing covering 50 is closely adhered to the outer surface of the main body stent 200.

Further, the vascular stent further includes a branch stent 300, and one end of the branch stent 300 passes through the secondary blood flow opening 54 on the sealing covering 50 and is inserted into the secondary body tube inner cavity 33 of the secondary body tube 30.

In this embodiment, two sealing body inner cavities 33 and one main body tube inner cavity 25 are disposed on the sealing covering 50 at the distal end of the vascular shunt frame 100. The main body stent 200 is inserted into the main body tube inner cavity 25; the positioning rod 70 is closely attached to the outer surface of the main body stent 200; a branch stent 300 is inserted into each secondary body tube inner cavity 33.

The main body stent 200 includes a connection covering 201 and a connection support frame 202 fixed on the connection covering 201. The structure of the main body stent 200 may be an equal-diameter stent-type blood vessel, or a non-equal-diameter stent-type blood vessel. As shown in FIG. 25a, the equal-diameter stent-type blood vessel means that the diameters of the main body stent 200 at different positions in the axial direction are the same. As shown in FIG. 25b, the non-equal-diameter stent blood vessel means that the diameters of the main body stent 200 at different positions in the axial direction are different. The non-equal-diameter stent-type blood vessel is a non-equal-diameter stent composing, from the proximal end to the distal end in sequence, a first tubular body 210, a second tubular body 220, and a third tubular body 230; the diameter of the second tubular body 220 is smaller than that of the first tubular body 210 and that of the third tubular body 230. A transition portion 221 and a transition portion 222 may be further disposed between the first tubular body 210, the second tubular body 220, and the third tubular body 230. As shown in FIG. 25c, a part of the support frame 202 at the proximal end of the main body stent 200 is exposed outside the covering 201, and is used to connect the conveying device. As shown in FIG. 25d, the main body stent 200 is a non-equal-diameter stent; the diameter of the proximal end of the non-equal-diameter stent is greater than the diameter of the distal end, and the diameter gradually decreases from the proximal end to the distal end. The entire support forms a uniform round table structure with smooth transition, to adapt to the morphology of blood vessels with a diameter gradually changing from the proximal end to the distal end.

The connection covering 201 is made of polyester cloth, PTFE, PET or other polymer materials. The connection covering 201 of the equal-diameter stent-type vessel is straight, and the connection covering 201 of the non-equal-diameter stent-type vessel is a tubular structure with different axial diameters.

The main body stent 200 may be a high-low wave stent-type blood vessel or a high-wave stent-type blood vessel. As shown in FIG. 25c, the high-low wave stent-type blood vessel is a partially sutured stent. The connection support frame 202 is sutured to the connection covering 201 by a suture. The specific suturing method is the same as the suturing method between the main body tube covering 22 and the main body tube support frame 24 of the vascular shunt frame 100 described above, which is not repeated here. The embedded branch surface is a high wave array surface of an annular wave-shaped supporting rod, and the center line of the embedded branch corresponds to the center line of the high wave. When the main body stent 200 is inserted into the vascular shunt frame 100, the high wave surface can provide a radial support force, and the low wave surface provides better flexibility to facilitate conforming to the structure of the aortic arch.

The structure of the branch stent 300 is the same as the structure of the main body stent 200, and details are not described herein again.

When in use, one first releases the vascular shunt frame 100 in the body, observes and determines the releasing position of the vascular shunt frame 100 by an imaging equipment; then releases the proximal end of the main body stent 200 into the main blood flow opening 52 of the main body tube inner cavity 25 at the distal end of the vascular shunt frame 100. Because the diameter of the main blood flow opening 52 of the main body tube inner cavity 25 is smaller than the diameter of the proximal portion of the main body stent 200 after releasing, therefore, the positioning rod 70 presses the proximal portion of the main body stent 200, such that the tubular body of the main body stent 200 is closely attached to the sealing covering 50 at the distal end of the main body tube 20 to prevent endoleaks. Then the proximal end of the branch stent 300 is released into the secondary blood flow opening 54 of the secondary body tube inner cavity 33 at the distal end of the vascular shunt frame 100; the proximal end of the branch vascular stent 300 is inserted into the secondary body tube inner cavity 33 along the inclined surface of the sealing covering 50, so as to facilitate the insertion of the branch vascular stent 300. Because the diameter of the secondary blood flow opening 54 of the secondary body tube inner cavity 33 is smaller than the diameter of the proximal portion of the branch vascular stent 300 after releasing, therefore, the secondary body tube inner cavity 33 presses the proximal portion of the branch stent 300 such that the tubular body of the branch stent 300 fits the wall of the secondary body tube inner cavity 33 to prevent endoleaks. Because a radiopaque structure 80 is disposed at both the main blood flow opening 52 of the main body tube inner cavity 25 of the vascular shunt frame 100 and the secondary blood flow opening 54 of the secondary body tube inner cavity 33, the main body stent 200 and the branch vascular stent 300 can be easily inserted.

In a further embodiment, the vascular stent can be used for the treatment of thoracic aortic aneurysm or thoracic aortic dissection disease, and is particularly suitable for the treatment of thoracic aortic aneurysm or thoracic aortic dissection disease involving the ascending aorta or aortic arch. As shown in FIG. 24, when releasing, one pushes the delivery device along the super-hard guide wire to push the pre-installed vascular shunt frame 100 to the position of the thoracic aortic dissection; one locates by the development ring at the front end of the sheath tube and the radiopaque structure 80 at the distal end of the vascular shunt frame 100, and releases the vascular shunt frame 100 by operating the handle of the delivery device; then one releases the main body stent 200 according to the same steps, such that the proximal end of the main body stent 200 is inserted into the main body tube inner cavity 25 of the vascular shunt frame 100; after expansion, the proximal end of the main body stent 200 is stuck by the positioning rod 70 and the main blood flow opening 52 to form a tight cooperation, thereby preventing the main body stent 200 from detaching from the vascular shunt frame 100. Finally, the same steps are followed to release the branch stent 300.

As shown in FIG. 24, the main body stent 200 may further is provided with a blood flow opening 205, and a branch vascular stent is inserted into the blood flow opening 205.

On the other hand, some of the main body stents 200 or the branch stents 300, from the distal end to the proximal end in sequence, are non-equal-height annular wave-shaped supporting rods. One to four peaks and/or valleys not sutured to the covering are disposed at the distal end or the proximal end of the stent graft of the annular stents; the peaks and/or valleys are bare stents for convenience of assembly. The number of each annular stent is set according to the axial length of the stent graft.

The above is the implementation of the embodiments of the present disclosure. It should be noted that, for those of ordinary skill in the art, without departing from the principle of the embodiments of the present disclosure, several improvements and modifications can be made. These improvements and modifications are also regarded as within the scope of protection of the present disclosure.

What is claimed is:

1. A vascular shunt frame with improved apposition, comprising a main body tube,
wherein
the main body tube includes a terminal end,
at least one end face of the main body tube is provided at the terminal end and is provided with a sealing covering,
the main body tube comprises a tubular main body covering,
the sealing covering is in a sealed connection with the tubular main body covering at the at least one end face,
the sealing covering is provided with a main blood flow opening, and
an edge of the main blood flow opening is provided with a shaping component, wherein the shaping component is a positioning rod, and the positioning rod is fixed to the sealing covering on the edge of the main blood flow opening away from a side of a side wall of the main body tube.

2. The vascular shunt frame according to claim 1, wherein the positioning rod extends along the edge of the main blood flow opening connected with the side of the side wall of the main body tube on the sealing covering towards a center of the main body tube; two opposite ends of the positioning rod are respectively connected to the side wall of the main body tube at different positions.

3. The vascular shunt frame according to claim 1, wherein the positioning rod is a linear rod, a wavy rod, or a curved rod.

4. The vascular shunt frame according to claim 1, wherein the positioning rod is composed of three connected circular arc rods; the positioning rod comprises a first circular arc rod located in a middle of the positioning rod, and two second circular arc rods connected to two opposite ends of the first circular arc rod; and wherein the two second circular arc rods are symmetrical along a middle point of the first circular arc rod.

5. The vascular shunt frame according to claim 4, wherein a middle portion of the first circular arc rod is bent toward the main blood flow opening, and a middle portion of each of the second circular arc rods is bent toward a side away from the main blood flow opening.

6. The vascular shunt frame according to claim 1, wherein at least one secondary blood flow opening is disposed on the sealing covering; at least one secondary tube is disposed in the main body tube; the at least one secondary body tube is connected to a respective one of the at least one secondary blood flow opening, and the at least one secondary blood flow opening and the main blood flow opening are arranged at an interval.

7. The vascular shunt frame according to claim 6, wherein the sealing covering is provided with at least one supporting component, and the at least one supporting component is connected between the shaping component and an edge of the at least one secondary blood flow opening adjacent to the shaping component.

8. The vascular shunt frame according to claim 7, wherein each of the at least one supporting component is a supporting rod fixed to the sealing covering; one end of the supporting rod is connected to the shaping component and another end of the supporting rod is connected to the edge of the at least one secondary blood flow opening adjacent the shaping component.

9. The vascular shunt frame according to claim 8, wherein the at least one secondary blood flow opening comprises two tangential secondary blood flow openings and the at least one supporting rods is connected between the shaping component and a tangential point of the two tangential secondary blood flow openings.

10. The vascular shunt frame according to claim 8, wherein the at least one supporting component comprises two supporting components, which are respective ones of the supporting rods, the two supporting rods are fixedly spaced on the sealing covering, and the two supporting rods are respectively connected between the edge of the at least one secondary blood flow opening and the shaping component.

11. The vascular shunt frame according to claim 8, wherein the at least one supporting component comprises three supporting components, which are respective ones of the supporting rods, the three supporting rods are fixedly spaced on the sealing covering; one of the three supporting rods is in a middle and connected between the at least one secondary blood flow opening and a middle portion of the shaping component; the remaining two supporting rods of the three supporting rods are on each side of the one supporting rod and are respectively connected between the edge of the at least one secondary blood flow opening and two opposite ends of the shaping component.

12. The vascular shunt frame according to claim 8, wherein the at least one supporting component comprises four supporting components, which are respective ones of the supporting rods, the four supporting rods are fixedly spaced on the sealing covering; two of the four supporting rods are in a middle and connected between respective ones of the at least one secondary blood flow opening and a middle portion of the shaping component; the remaining two supporting rods of the four supporting rods are on a side opposing respective ones of the two supporting rods and are respectively connected between the edge of the at least one secondary blood flow opening and two opposite ends of the shaping component.

13. The vascular shunt frame according to claim 8, wherein the at least one supporting rod comprises a first rod body and a second rod body inclinedly connected to one end of the first rod body; the first rod body is fixed to the sealing covering; the second rod body is fixed on a side wall of at least one secondary body tube; an intersection between the first rod body and the second rod body is located at an intersection between the sealing covering and the side wall of the at least one secondary body tube; one end of the first rod body, away from the second rod body, is connected to the shaping component.

14. The vascular shunt frame according to claim 6, wherein at least an end face of a distal end of the at least one secondary blood flow opening is lower than an end face of a distal end of the main blood flow opening; the sealing covering is recessed toward the at least one secondary blood flow opening such that the sealing covering and the side wall of the main body tube form a bell mouth opening.

15. The vascular shunt frame according to claim 6, wherein an edge of at least one of the at least one secondary blood flow opening and/or the main blood flow opening is provided with a radiopaque structure, the radiopaque structure is radiopaque markers continuously or intermittently fixed to an edge of the sealing covering on any of the at least one of the at least one secondary blood flow opening or the main blood flow opening.

16. The vascular shunt frame according to claim 15, wherein the radiopaque structure comprises a supporting component and a radiopaque component, and the supporting component is a metal ring or a metal rod adapted to a shape of the edge of the main blood flow opening or the at least one secondary blood flow opening, the radiopaque component is selected from the group consisting of a radiopaque wire continuously o intermittently wound around the metal ring or the metal rod; a radiopaque marker inlaid or pasted on a periphery or a surface of the metal rod; and a radiopaque material fused within the metal ring or the metal rod.

17. A vascular stent comprising a main body stent, wherein the vascular stent further comprises a vascular shunt frame according to claim 1; one end of the main body stent passes through the main blood flow opening on the sealing covering and is inserted into the main body tube of the vascular shunt frame; the shaping component positions the main body stent such that the sealing covering closely adheres to an outer surface of the main body stent.

18. The vascular stent according to claim 17, wherein a secondary blood flow opening is disposed on the sealing covering, the vascular shunt frame further comprises a secondary body tube disposed in the main body tube, and the vascular stent further comprises a branch stent, and one end of the branch stent passes through the secondary blood flow opening on the sealing covering and is inserted into the secondary body tube of the vascular shunt frame.

19. A vascular shunt frame with improved apposition, comprising a main body tube, wherein
the main body tube includes a terminal end,
at least one end face of the main body tube is provided at the terminal end and is provided with a sealing covering,
the main body tube comprises a tubular main body covering,
the sealing covering is in a sealed connection with the tubular main body covering at the at least one end face,
the sealing covering is provided with a main blood flow opening, and
an edge of the main blood flow opening is provided with a shaping component,
wherein at least one secondary blood flow opening is disposed on the sealing covering; at least one secondary body tube is disposed in the main body tube; the at least one secondary body tube is connected to the at least one secondary blood flow opening, and the at least one secondary blood flow opening and the main blood flow opening are arranged at an interval; and
wherein the sealing covering is provided with at least one supporting component, which is connected between the shaping component and an edge of the at least one secondary blood flow opening adjacent to the shaping component.

20. A vascular stent comprising a main body stent and at least one branch stent, wherein the vascular stent further comprises a vascular shunt frame according to claim 19; one end of the main body stent passes through the main blood flow opening on the sealing covering and is inserted into the main body tube of the vascular shunt frame; the shaping component positions the main body stent such that the sealing covering closely adheres to an outer surface of the main body stent, and
wherein one end of each of the at least one branch stent passes through a respective one of the at least one secondary blood flow opening and is inserted into a respective one of the at least one secondary body tube.

* * * * *